(12) United States Patent
Miller et al.

(10) Patent No.: US 8,450,056 B2
(45) Date of Patent: May 28, 2013

(54) ARRAYED IMAGING REFLECTOMETRY (AIR) SENSOR CHIP COMPRISING VIRUS-LIKE PARTICLES SUITABLE FOR THE DETECTION OF ANTIVIRAL IMMUNE RESPONSES

(75) Inventors: Benjamin L. Miller, Penfield, NY (US); Tim R. Mosmann, Pittsford, NY (US); Robert C. Rose, Geneseo, NY (US); Charles R. Mace, Auburn, NY (US)

(73) Assignee: University of Rochester, Rochester, NY (US)

( * ) Notice: Subject to any disclaimer, the term of this patent is extended or adjusted under 35 U.S.C. 154(b) by 747 days.

(21) Appl. No.: 12/434,298

(22) Filed: May 1, 2009

(65) Prior Publication Data

US 2010/0075300 A1    Mar. 25, 2010

Related U.S. Application Data

(60) Provisional application No. 61/050,065, filed on May 2, 2008.

(51) Int. Cl.
| | | |
|---|---|---|
| *C12Q 1/70* | (2006.01) | |
| *G01N 33/552* | (2006.01) | |
| *G01N 33/549* | (2006.01) | |
| *G01N 21/00* | (2006.01) | |
| *G01B 9/02* | (2006.01) | |

(52) U.S. Cl.
USPC .............. 435/5; 436/527; 436/532; 436/164; 422/82.05; 356/450; 424/186.1; 424/199.1; 424/204.1; 424/206.1; 424/208.1; 424/211.1

(58) Field of Classification Search
None
See application file for complete search history.

(56) References Cited

U.S. PATENT DOCUMENTS

| | | | |
|---|---|---|---|
| 7,292,349 B2 | 11/2007 | Miller et al. | |
| 7,455,972 B2 | 11/2008 | Virgin | |
| 2003/0073245 A1* | 4/2003 | Shinoki et al. | ............ 436/173 |
| 2004/0224305 A1* | 11/2004 | Wilson et al. | ............ 435/5 |
| 2006/0257852 A1 | 11/2006 | Rappuoli et al. | |
| 2006/0263804 A1 | 11/2006 | Robinson et al. | |
| 2007/0076214 A1 | 4/2007 | Rothberg | |
| 2007/0212375 A1 | 9/2007 | Caston et al. | |
| 2007/0218459 A1 | 9/2007 | Miller et al. | |
| 2008/0031895 A1 | 2/2008 | Galarza et al. | |
| 2009/0153867 A1* | 6/2009 | Mace et al. | ............ 356/445 |

OTHER PUBLICATIONS

Beare et al., "Candidate Antigens for Q Fever Serodiagnosis Revealed by Immunoscreening of a *Coxiella burnetti* Protein Microarray," Clin Vaccine Immunol 15:1771-1779 (2008).
Mace et al., "A Theoretical and Experimental Analysis of Arrayed Imaging Reflectometry as a Sensitive Proteomics Technique," Anal Chem 78:5578-5583 (2006).
Horner et al., "A Proteomic Biosensor for Enteropathogenic *E. coli*," Biosensors and Bioelectronics 21:1659-1663 (2006).
Mace et al., "Detection of Human Proteins Using Arrayed Imaging Reflectometry," Biosensors and Bioelectronics 24:334-337 (2008).
Duthie et al., "Selection of Antigens and Development of Prototype Tests for Point-of-Care Leprosy Diagnosis," Clin Vaccine Immunol 15:1590-1597 (2008).
Xu et al., "Profiling the Humoral Immune Response to *Borrelia burgdorferi* Infection with Protein Microarrays," Microbial Pathogenesis 45:403-407 (2008).
Whelan et al., "Multiplex Immunoassay for Serological Diagnosis of *Myobacterium bovis* Infection in Cattle," Clin Vaccine Immunol 15:1834-1838 (2008).
International Search Report dated Mar. 3, 2010 for PCT/US2009/42531.

* cited by examiner

*Primary Examiner* — Jeffrey Parkin
(74) *Attorney, Agent, or Firm* — LeClairRyan, a Professional Corporation

(57) ABSTRACT

A sensor chip for detecting an immune response against a virus, the sensor chip including a substrate having a surface and a plurality of virus-like particles or capsid fragments bound to discrete locations on the surface of the substrate. Detection devices containing the sensor chip and methods of detecting anti-viral immune responses are also described herein.

10 Claims, 5 Drawing Sheets

SPR OUTPUT $d \ll \lambda$ $d < \lambda$, almost a rough 'layer'

$d < \lambda$, discrete objects

US 8,450,056 B2

ARRAYED IMAGING REFLECTOMETRY (AIR) SENSOR CHIP COMPRISING VIRUS-LIKE PARTICLES SUITABLE FOR THE DETECTION OF ANTIVIRAL IMMUNE RESPONSES

This application claims the benefit of U.S. Provisional Patent Application Ser. No. 61/050,065, filed May 2, 2008, which is hereby incorporated by reference in its entirety.

This invention was made with government support under grant number R24-AL054953 awarded by the National Institutes of Health. The government has certain rights in this invention.

FIELD OF THE INVENTION

This invention relates to sensor chips designed for the detection of an immune response to a particular antigen, which can be used either to detect an individual's prior exposure to a pathogen that possesses the antigen, for epidemiological purposes to survey the extent of infection among a population of individuals, or to measure the efficacy of a vaccine directed against the pathogen.

BACKGROUND OF THE INVENTION

The development of rapid, sensitive, simple to use, and inexpensive biosensors is of significant continuing interest to applications ranging from medical diagnostics to biowarfare agent detection. Over the past five years, a technique has been developed termed "Arrayed Imaging Reflectometry", or AIR, that relies on the initial creation of a near-null reflectance condition in a thin film on the surface of a reflective substrate. When illuminated with s-polarized light at a wavelength and angle tuned to the material system used, perturbation of this near-null reflectance condition due to target binding is readily observed as an increase in the reflected intensity. This allows for parallel detection of analytes with high sensitivity and dynamic range. AIR employs an exceptionally simple detection system, containing a single-wavelength light source such as a helium-neon laser (an ideal wavelength for AIR chips based on silicon/silicon dioxide), a set of optics to polarize, expand, and collimate the beam, a fixed sample stage, and a CCD camera. To date, AIR has been employed for the detection of oligonucleotides (Lu et al., "Reflective Interferometric Detection of Label-free Oligonucleotides," *Anal Chem* 76:4416-4420 (2004)), proteins derived from pathogenic *E. coli* (Mace et al., "A Theoretical and Experimental Analysis of Arrayed Imaging Reflectometry as a Sensitive Proteomics Technique," *Anal Chem* 78:5578-5583 (2006)) as well as O15:H-*E. coli* itself (Horner et al., "A Proteomic Biosensor for Enteropathogenic *E. Coli*," *Biosensors and Bioelectronics* 21:1659-1663 (2006)), and human cytokines (Mace et al., "Detection of Human Proteins Using Arrayed Imaging Reflectometry," *Biosensors and Bioelectronics* 24:334-337 (2008)). The latter also allowed the demonstration of the suitability of employing AIR for detection of proteins in human serum, a challenging milieu for any label-free biodetection system.

Direct detection of pathogen-derived proteins or nucleic acids is obviously of crucial importance for the development of diagnostics. However, one can also detect the traces of the human body's exposure to a pathogen through the immune response: specific antibodies to pathogen-derived antigens are potentially useful as an indicator of exposure, and of immunity. So-called "antigen arrays" have been employed for a wide range of diseases, and recent examples include organisms responsible for leprosy (Duthie et al., "Selection of Antigens and Development of Prototype Tests for Point-of-Care Leprosy Diagnosis," *Clin Vaccine Immunol* 15:1590-1597 (2008)), Lyme disease (Xu et al., "Profiling the Humoral Immune Response to *Borrelia burgdorferi* Infection with Protein Microarrays," *Microbial Pathogenesis* 45:403-407 (2008), bovine tuberculosis (Whelan et al., "Multiplex Immunoassay for Serological Diagnosis of *Myobacterium bovis* Infection in Cattle," *Clin Vaccine Immunol* 15:1834-1838 (2008), and Q fever (Beare et al., "Candidate Antigens for Q Fever Serodiagnosis Revealed by Immunoscreening of a *Coxiella burnetti* Protein Microarray," *Clin Vaccine Immunol* 15:1771-1779 (2008)).

Detection of soluble proteins is fundamental to many aspects of immunology, but it is still a challenge for one method to achieve high sensitivity, robustness with biological fluids, multiplexing of many related analytes, in a rapid detection method with low costs. Array-based optical techniques for specific protein detection have the potential to address all of these objectives. Using specific capture antibodies, it is possible to detect very low concentrations of proteins with high specificity in a very rapid assay. Another major advantage is that no labeled detection reagents are needed, i.e., the analyte is detected directly.

It would be desirable to provide an array of immobilized antigens that can be used to screen for antibodies against infectious agents and vaccines involving multiple similar specificities, e.g., distinguishing between different strains of an infectious agent such as a virus, based on the immune response generated by these infectious agents.

The present invention is directed to overcoming this and other deficiencies in the art.

SUMMARY OF THE INVENTION

A first aspect of the present invention relates to a sensor chip for detecting an immune response against a virus. The sensor chip includes a substrate having a surface and a plurality of virus-like particles (VLPs) or capsid fragments that present conformational epitopes of the whole virus, which VLPs or capsid fragments are bound to discrete locations on the surface of the substrate.

A second aspect of the present invention relates to a detection system that includes a sensor chip according to the first aspect of the present invention, a light source that is positioned to illuminate the chip, and a detector that is positioned to detect light reflected from the surface of the chip, and thereby determine whether an antibody binds to the VLP or capsid fragment.

A third aspect of the present invention relates to a flow cell that includes a base having an inlet and an outlet; a light transmissive cover mounted to the base in a substantially fluid-tight manner, and forming with the base a compartment through which fluid may pass from the inlet to the outlet; and a sensor chip according to the first aspect of the present invention. The sensor chip is positioned in the compartment and exposed through the light transmissive cover to incident light, whereby incident light used to illuminate the chip surface at an appropriate angle of incidence achieves a condition of near perfect destructive interference in the absence of antibody binding to a VLP or capsid fragment.

A fourth aspect of the present invention relates to a detection system that includes: a flow cell according to the third aspect of the present invention; a fluid sample source in fluid communication with the inlet of the flow cell; a light source that is positioned to illuminate the chip; and a detector that is positioned to detect light reflected from the surface of the chip. The angle of incidence of the illuminating light is suitable to produce a condition of near perfect destructive interference in the absence of antibody binding to a VLP or capsid fragment, and a substantial change in light reflectivity in the presence of antibody binding to a VLP or capsid fragment.

A fifth aspect of the present invention relates to a method for sensing an anti-viral antibody. This method includes the steps of: providing a detection system according to the second aspect of the present invention; directing light at a surface of the sensor chip; contacting the sensor chip with a sample under conditions effective to allow an anti-viral antibody in the sample to bind specifically to a VLP or capsid fragment recognized by the antibody; and detecting light reflected from the chip under conditions effective to identify VLPs or capsid fragment bound by an antibody of the sample.

A sixth aspect of the present invention relates to a method for sensing an anti-viral antibody. This method includes the steps of: providing a detection system according to the fourth aspect of the present invention; directing light at the sensor chip in a manner effective to result in a condition of near perfect destructive interference; introducing a fluid sample into the flow cell; measuring light reflected from the chip; and providing an output identifying the VLPs or capsid fragments bound by an antibody of the fluid sample based on the measured reflected light.

A seventh aspect of the present invention relates to a method for screening efficacy of a virus vaccine. This method includes the steps of administering a virus vaccine to one or more individuals; obtaining a serum sample for the one or more individuals; and performing the method according to fifth or sixth aspects of the present invention to measure the anti-viral immune response generated by the vaccine.

The present invention provides an array of immobilized VLPs or capsid fragments that can be used to screen for antibodies against infectious agents and vaccines involving multiple similar specificities. The arrays of the present invention, when used with an appropriate detection system, can multiplex many related but distinct analytes while achieving high sensitivity and maintaining robustness of biological fluids. Use of these arrays and detection systems affords a rapid detection method with low costs, and can be performed using "label-less" reagents.

AIR is a new label-free technique for detecting proteins that relies on binding-induced changes in the response of an antireflective coating on the surface of a sensor chip. Because the technique provides high sensitivity, excellent dynamic range, and readily integrates with standard silicon wafer processing technology, it is an exceptionally attractive platform on which to build systems for detecting proteins in complex solutions. Unlike early uses of AIR where a pathogen was detected directly, the present invention demonstrates that an alternative strategy can be used effectively: immobilizing antigens from a pathogen and employing AIR to detect antibody responses to those antigens. In principle, such a strategy provides enhanced sensitivity for pathogen detection (as the immune system essentially amplifies the "signal" caused by the presence of an organism to which it responds), and should prove useful in the process of vaccine development.

As an initial demonstration of an AIR-based sensor for pathogen-specific antibodies, the utility of chips bearing virus-like particles corresponding to two variants of human papillomavirus (HPV) was examined. HPV is a broadly distributed human pathogen that is responsible for up to 5% of all human cancers worldwide (Moscicki et al., "HPV Vaccines: Today and in the Future," *J Adolescent Health* 43:S26-S40 (2008), which is hereby incorporated by reference in its entirety) and in particular is believed to be the major causative agent of cervical cancer (Schiffman et al., "Epidemiologic Evidence Showing that Human Papillomavirus Infection Causes Most Cervical Intraepithelial Neoplasia," *J Nat Cancer Inst* 85:958-964 (1993), which is hereby incorporated by reference in its entirety). Estimates of the prevalence of cervical cancer vary, but are on the order of 500,000 new cases worldwide per year (Echchannaoui et al., "Intravaginal Immunization of Mice with Recombinant *Salmonella enterica serovar* Typhimurium Expressing Human Papillomavirus Type 16 Antigens as a Potential Route of Vaccination Against Cervical Cancer," *Infect Immun* 76:1940-1951 (2008), which is hereby incorporated by reference in its entirety).

The HPV viral coat is formed by self-assembly of a single protein, termed L1. When L1 is expressed independently of the remainder of the virus, it retains the ability to assemble into a roughly 50 nm diameter icosahedral structure termed a virus-like particle, or VLP. VLPs derived from HPV have been studied for some time as immunogenic models for the virus, and in particular are the primary constituents of the commonly used HPV vaccine GARDASIL®. GARDASIL® is a mixture of VLPs derived from four different HPV genotypes (Monie et al., "Preventive and Therapeutic HPV Vaccines," *Curr Opin Investig Drugs* 8:1038-1050 (2007), which is hereby incorporated by reference in its entirety), a consequence of the observation that different VLPs are antigenically distinct (Rose et al., "Serological Differentiation of Human Papillomavirus Types 11, 16, and 18 Using Recombinant Virus-like Particles," *J Gen Virol* 75:1445-1449 (1994), which is hereby incorporated by reference in its entirety). Preliminary efforts were focused on VLPs derived from HPV genotype 11, a major agent of benign anogenital warts, and HPV genotype 16, the most prevalent of the oncogenic HPV genotypes.

DETAILED DESCRIPTION OF THE INVENTION

One aspect of the present invention concerns a sensor chip that is useful for detecting an immune response against a virus or its vaccine. The sensor chip includes a substrate having a surface and a plurality of VLPs or capsid fragments that present conformational epitopes of the whole virus. The VLPs or capsid fragments are bound to discrete locations on the surface of the substrate. Each VLP or capsid fragment is conformationally correct, preferably containing immunodominant epitope(s) of the native virion that it is intended to mimic.

The overall design and construction of the sensor chip can be varied according to the particular detection system in which it is to be employed. These include, for example and without limitation, sensors designed for use with AIR detection systems, SPR detection systems, BASI detection systems, and ellipsometry detection systems, as well as any other label-free or fluorescence labeled array technique.

Figure 1:
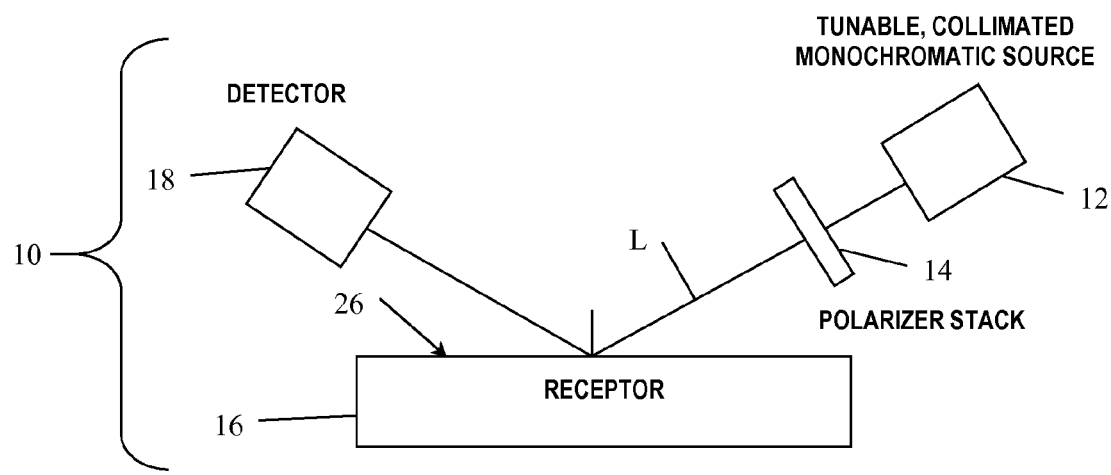
FIG. 1 is a schematic illustration of an AIR detection system.

An AIR detection system is described in U.S. Pat. No. 7,292,349 to Miller et al., which is hereby incorporated by reference in its entirety. This system is illustrated in FIG. 1. The system 10 includes a light source 12, a polarizer 14, a receptor 16 (i.e., the functionalized sensor chip of the present invention), and a detector 18. The light source 12 generates and transmits light (L) at a set wavelength towards a surface of the receptor. One or more lenses and filters can be employed to optimize the system. AIR exploits interference between reflections from the medium/coating and coating/substrate interfaces on the receptor, exhibiting changes in reflectivity upon binding of biomolecules to the coating. In practice, using a silicon wafer having an oxide coating, judicious choice of incident angle and wavelength can be used with s-polarized light to obtain near complete destructive interference (i.e., reflectivity that is preferably less than about $10^{-5}$ or even $10^{-6}$ under some circumstances) in the absence of a target, in this case the anti-VLP antibodies. The condition of near complete (or near perfect) destructive interference is removed upon target binding. Thus, highly sensitive detection of even small quantities of anti-VLP antibodies is possible.

While AIR using s-polarized light has proven to be a highly sensitive, simple analytical method for the quantitative detection of a variety of biomolecular analytes, the system described in the above-referenced U.S. Pat. No. 7,292,349 to Miller et al. is much more easily carried out in a dry state, that is, with an air/oxide interface rather than with an aqueous/oxide interface. An improved system for performing AIR in an aqueous environment is described in co-pending U.S. patent application Ser. No. 12/261,818 to Mace et al., and PCT International Patent Application No. PCT/2008/081804 to Mace et al., which are hereby incorporated by reference in their entirety. Basically, the flow cell as described therein allows for coupling of the s-polarized light into the aqueous environment for detection of target binding. Use of this same flow cell, containing a sensor chip functionalized with the plurality of VLPs, is contemplated herein.

Figure 2:
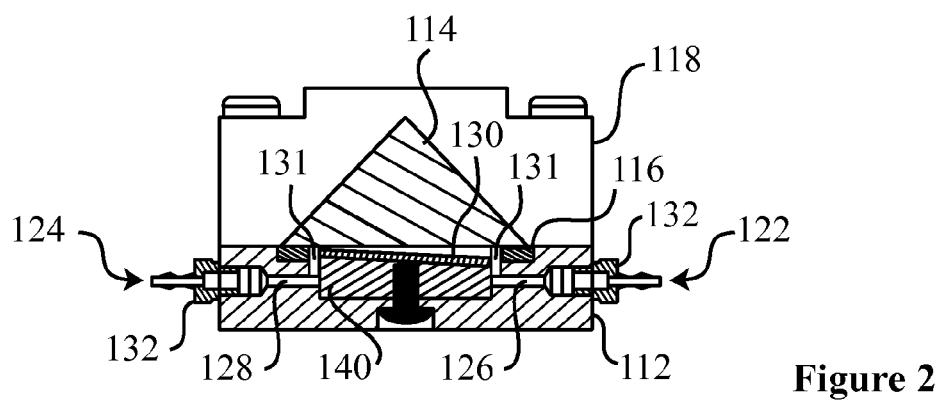
FIG. 2 is a cross-sectional view a flow cell of the invention which includes a sensor chip suitable for use in an AIR detection system for aqueous environments.

The flow cell is illustrated in FIG. 2. The flow cell includes a base 112, a light transmissive cover 114 in the form of a 90° prism, a gasket 116 positioned between the base and cover, and one or more mounting braces 118 that are utilized to secure the base and cover in a substantially fluid-tight manner. The base 112 includes a well 120 formed in one face thereof, as well as inlet 122 and outlet 124 that communicate with the well via passages 126 and 128, respectively. Inlet 122 and outlet 124 are formed on opposite ends of the base such that the passages 126 and 128 that communicate with the well 120 ensure fluid flow over chip 130 when it is placed in the well. To assist with fluid flow in this respect, a notch 131 is formed in the sidewall of well 120 at each end of the well such that fluid can easily flow into the well from passage 126 and from the well via passage 128. The passages 126 and 128 are preferably provided with fittings 132 that allow conduits or other forms of tubing to be coupled to the flow cell. For example, the fluid sample source can be coupled to the inlet 122 and the outlet 124 can be coupled to additional fluid analyzers or simply to a waste reservoir. The chip 130 is preferably supported in the well 120 by an angled chip support 140.

In both the wet and dry AIR systems, the sensor chip has the same fundamental construction, with a substrate, one or more coating layers on the substrate, and then the probe molecules—in this case the VLPs or capsid fragments—bound to the coating surface. As described in the above-referenced U.S. Pat. No. 7,292,349 to Miller et al., U.S. patent application Ser. No. 12/261,818 to Mace et al., and PCT International Patent Application No. PCT/2008/081804 to Mace et al., a number of different materials can be selected for the substrate and coating(s). Any suitable combination of substrates and coatings is contemplated for the sensor chip to be used in an AIR detection system.

The BASI detection system is described in U.S. Patent Publication No. 20070076214 to Rothberg, which is hereby incorporated by reference in its entirety. The BASI system, like the AIR system, exploits interference between reflections from the medium/coating and coating/substrate interfaces, and exhibits changes in reflectivity upon binding of biomolecules to the coating. The basic design of the system is similar to that illustrated in FIG. 1 (for AIR), but the structure of the sensor chip differs. The BASI system is functional with any substrate/coating combinations where the coating is very thin (e.g., a native oxide film on silicon) and when the incidence angle on one of two interfaces (substrate/coating or coating/medium) is greater than its Brewster angle and the incidence angle on the other of the two interfaces is less than its Brewster angle. Unlike AIR systems being commercially developed for use with incident s-polarized light, the BASI system relies on the detection with p-polarized light. As a result of using Brewster angle straddle and p-polarized light, where the coating thickness is $<<\lambda$, a phase flip of the reflected polarization allows nearly complete destructive interference (where reflectivity is preferably less than about $10^{-4}$ or even $10^{-5}$ in the absence of target binding). As with the AIR detection system, sensitive detection of even small quantities of anti-VLP antibodies is possible.

Figure 3:
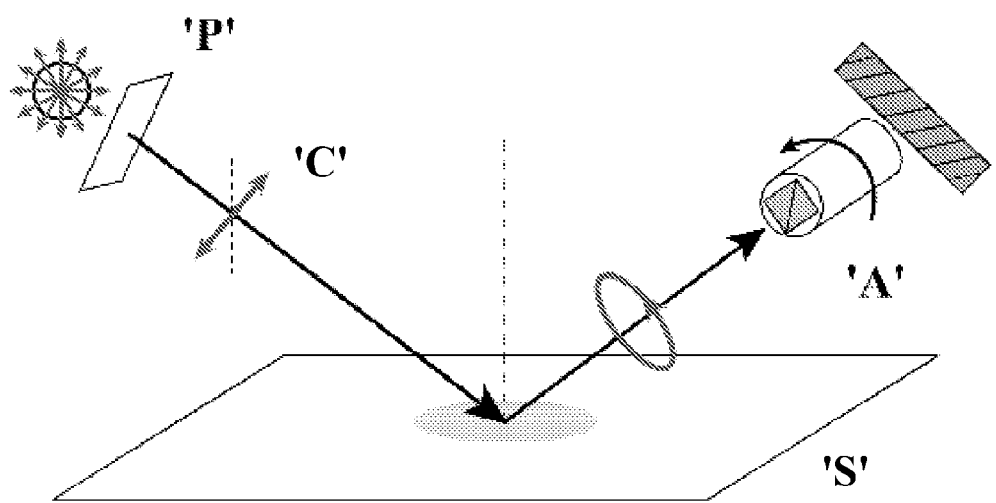
FIG. 3 is a schematic illustration of an ellipsometry detection system.

Ellipsometric detection systems measure the polarization component of reflected light as a measure of changes in coating thickness on the surface of the sensor chip. Ellipsometry sensitively measures the change of the state of polarization when electromagnetic radiation is reflected or transmitted by a sample. A classical embodiment of such an ellipsometric detection system, illustrated in FIG. 3, includes a light source that emits a collimated light beam passing a variable polarization controller given by the combination of a linear polarizer (P) and a compensator in the form of a quarter-wave plate (C). The polarized light beam is incident on the sensor surface (S) under a known oblique angle, reflected from the sample surface and analyzed by a second linear polarizer coupled to a suitable photodetector (A, collectively). In this ellipsometer setup, the measurement may be done by changing the azimuths of the components P and A, while the optical axis of C is kept at a constant azimuth, e.g., at 45° with respect to the plane of incidence, until the photodetector receives a minimum of intensity. The azimuthal angles of the components P, C and A for this "nulling" condition may be used to calculate the ellipsometric angles Delta and Psi, which are specific for the optical parameters of the sample at a given angle of incidence and wavelength of light. Using a suitable optical model and numerical regression, the quantities Delta and Psi may be recalculated in terms of the thickness of the optical layer, or changes thereof during a growth process. The application of ellipsometry for monitoring of binding reactions of biological molecules dates back to 1942 (Rothen et al., "Serological Reactions of Protein Films and Denatured Proteins," *J Exp Med* 76:437-450 (1942), which is herby incorporated by reference in its entirety), where the amount of adsorbed biological material at a surface during a binding reaction may be recalculated from the quantities Delta and Psi.

Imaging ellipsometry, as described for example in U.S. Pat. No. 5,076,696 to Cohn et al., which is hereby incorporated by reference in its entirety, uses spatially resolving detector and imaging optics to allow for a massively parallel measurement of ellipsometric data, e.g., in the form of Delta and/or Psi maps. Such maps may in turn be converted into surface maps of layer thickness, optical index of refraction, chemical composition or the amount of adsorbed material for each spot on an array. Imaging ellipsometry with its intrinsic parallel detection scheme may be used advantageously as a detection technique for these so-called biochips, microarrays or microplates (Eing et al., *Imaging Ellipsometry in Biotechnology*, ISBN 3-9807279-6-3 (2002), which is hereby incorporated by reference in its entirety).

Imaging ellipsometry has been demonstrated with light employed for the measurement impinging on the surface to be measured coming from the ambient medium. Other measurement setups are based on total internal reflection as described for example in U.S. Pat. No. 6,594,011 to Kempen, which is hereby incorporated by reference in its entirety. Here, the light from a light source is directed through an internal reflection element to reflect off the specimen to be detected.

Figure 4A:
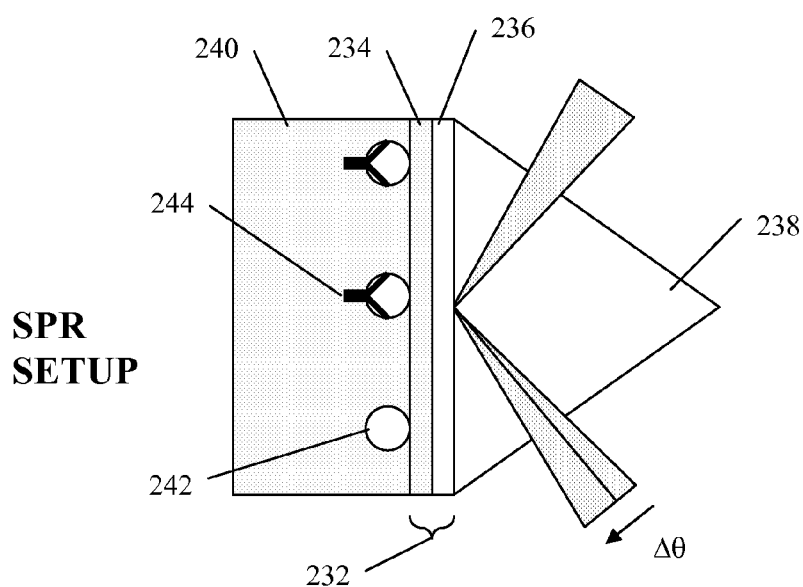
FIG. 4A is a schematic illustration of an SPR detection system.
Figure 4B:
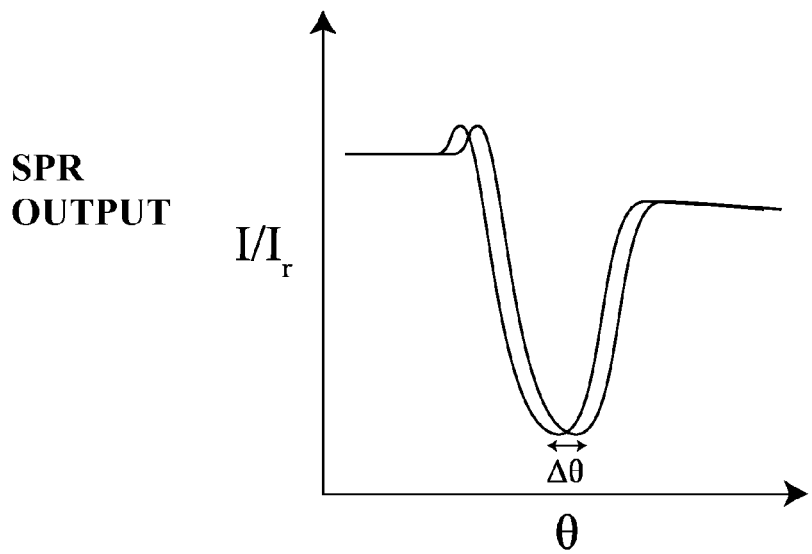
FIG. 4B illustrates the output of SPR.

Enhancement of the detection signal can be achieved using SPR ellipsometry, illustrated in FIG. 4A. The substrate 232 employed during SPR ellipsometry uses a thin metal layer 234 to allow the excitation and propagation of surface plasmons. While one side of the metal layer 234 is in contact with a transparent support structure 236, usually attached to a prism 238 allowing light to couple-in under an oblique angle, the other side of the layer is exposed to the ambient medium 240. Changes in the optical index of refraction in the ambient by the formation of an adsorbent layer (e.g., antibodies 244 binding to surface-bound VLP 242) are monitored as a shift in the angle of incidence ($\Delta\theta$) that generates surface plasmon resonance, causing a change of reflected light intensity (see FIG. 4B). For SPR based sensors it is known that an intermediate dielectric layer between the metal film and the probed surface may act as a means to further increase the sensitivity.

One exemplary SPR substrate is described in U.S. Pat. No. 7,332,329 to Wark et al., which is hereby incorporated by reference in its entirety. This SPR substrate is particularly suited for biomolecular arrays of VLPs, where the substrate includes a plurality of a metallic islands surrounded by a hydrophobic layer or a dielectric material, and the VLPs are bound to the metallic islands.

Regardless of the sensor chip substrate or the detection system in which the substrate is intended to be used, the sensor chip includes a plurality of VLPs or capsid fragments that present conformational epitopes of the whole virus. The VLPs or capsid fragments are bound to the surface of the sensor chip.

A trait inherent to all biosensors, regardless of labeling status or means of signal transduction, is probe immobilization. The role of the terminal hydroxyl of a silicon dioxide surface is highly flexible as it may act as a nucleophile (Bikiaris et al., "Compatibilisation Effect of PP-g-MA Copolymer on iPP/SiO2 Nanocomposites Prepared by Melt Mixing," *Eur Polym J* 41:1965-1978 (2005); Tripp et al., "Chemical Attachment of Chlorosilanes to Silica: a Two-step Amine-Promoted Reaction," *J Phys Chem* 97:5693-5698 (1993), each of which is hereby incorporated by reference in its entirety) or support adsorption. For this reason, silicon dioxide is readily derivitized through a variety of chemical methods. These chemical reactions result in the effective transformation of the hydroxyl group to any of a number of chemical functionalities including, but not certainly not limited to, amines (Huang et al., "Directed Assembly of One-dimensional Nanostructures into Functional Networks," *Science* 291: 630-633 (2001), which is hereby incorporated by reference in its entirety) or halides (Hergenrother et al., "Small-molecule Microarrays: Covalent Attachment and Screening of Alcohol-containing Small Molecules on Glass Slides," *J Am Chem Soc* 122: 7849-7850 (2001), which is hereby incorporated by reference in its entirety). From each initial reaction, a secondary chemical can be added to further alter the surface reactivity or probes may be directly coupled. Moreover, a multitude of functionalized silanes, molecules that couple to and self-assemble on silicon dioxide (Onclin et al., "Engineering Silicon Oxide Surfaces Using Self-assembled Monolayers," *Angew Chemie Int Ed* 44:2-24 (2005), which is hereby incorporated by reference in its entirety), are commercially available, and may confer a diverse chemical landscape to the surface of the substrate (amines, epoxides, alkenes, etc.). A number of these approaches are generally described in U.S. Pat. No. 7,226,733 to Chan et al. and U.S. Pat. No. 7,292,349 to Miller et al., each of which is hereby incorporated by reference in its entirety.

U.S. Provisional Patent Application Ser. No. 61/101,831 to Mace et al., which is hereby incorporated by reference in its entirety, teaches the use of a non-nucleophilic additive in a formulation containing a probe molecule to be bound to an array surface. The non-nucleophilic additive is used in an amount effective to avoid or reduce the severity of surface morphological anomalies caused by non-homogeneous distribution of the reactant across a spot on the array where the reactant is bound. These surface morphological anomalies include bright center spots and "coffee stain" rings (or halos) that can interfere with accurate detection of target molecule binding at a particular spot. In other words, the use of effective amounts of the non-nucleophilic additive promotes substantially homogeneous distribution of the reactant across each of the spots on the array where the probe is located. By homogeneous distribution, it is intended that the variance of reactant concentration across the surface of a spot is minimized (relative to spots prepared in the absence of the non-nucleophilic additives). Stated another way, there is preferably less than about 10 percent pixel variation across the array spot, more preferably less than 5 percent variation, most preferably less than about 3 percent variation, 2 percent variation, or even less than about 1 percent variation.

Any effective amount of non-nucleophilic additive can be used. Typically, such an effective amount is between about 0.001 to about 3 percent v/v, more preferably between about 0.01 to about 1 percent v/v.

One embodiment of the non-nucleophilic additive includes compounds having a structure of formula (I) as follows:

(I)

where, n is an integer from 0 to about 250; m is an integer from 1 to 3, preferably 1 or 2; and $R^1$ and $R^2$ are independently selected from the group of a C1 to C3 alkyl, or $R^1$ and $R^2$ together form a C1 to C3 alkyl, in which case the compound of formula (I) has a cyclic structure. $R^1$ and $R^2$ are preferably methyl or ethyl, or together form an ethyl group. These additives preferably have a molecular weight that is about 5000 Da or less, more preferably about 4000 Da or less, or about 3000 Da or less, most preferably about 2000 Da or less, or even about 1000 Da or less. Exemplary non-nucleophilic additives of formula (I) include, without limitation, crown ethers (18-Crown-6, 15-Crown-5, 12 Crown-4, etc.), bis(2-methoxyethyl) ether, dialkyl ethers, and polyethylene glycol.

According to another embodiment, the non-nucleophilic additive is dimethylsulfoxide (DMSO).

The benefit of employing the non-nucleophilic additives, which do not participate in the chemical coupling of a reactant (or probe precursor) to the functionalized chip substrate, is that these additives promote better dispersion of the probe molecules across their respective discrete locations on the array. This improved dispersion consequently minimizes or entirely avoids the presence of surface morphological anomalies that can decrease the sensitivity of the detection system. As a result, improved sensitivity for the detection of target molecules can be achieved.

As used herein, the term VLP refers to a structural assembly of at least one type of protein or glycoprotein of a virus, and possibly several proteins or glycoproteins of a virus, and which possesses at least one conformational epitope of the native virus that the VLP is intended immunologically to mimic. The term VLP is intended to encompass both VLPs that contain exclusively those proteins of the native virus that they are intended immunologically to mimic, as well as chimeric VLPs that utilize the structural coat of one virus to present an antigenic epitope of a different virus.

As used herein, the term "capsid fragments" refers to capsid subassemblies (capsomeres) or even individual proteins or polypeptides that possess conformational epitopes of the native virus. The capsid subassemblies may be formed of one or more different proteins, including chimeric proteins.

VLPs or capsid fragments bound to the surface of the sensor chip are preferably those that find use as components of anti-virus vaccines, although VLPs that are not present in vaccines can also be used. Regardless, the use of VLPs in vaccines is now becoming more widespread, and VLPs have been developed for a number of different viral pathogen. Exemplary VLPs include, without limitation, papillomavirus VLPs, particularly HPV VLPs (e.g., VLPs for HPV-11, -16, -18, -31, -33, -45, -58, and -59) (Rose et al., "Expression of Human Papillomavirus Type 11 L1 Protein in Insect Cells: in vivo and in vitro Assembly of Viruslike Particles," *J Virol* 67:1936-1944 (1993); Rose et al., "Human Papillomavirus (HPV) Type 11 Recombinant Virus-like Particles Induce the Formation of Neutralizing Antibodies and Detect HPV-specific Antibodies in Human Sera," *J Gen Virol* 75:2075-2079 (1994); Rose et al., "Serological Differentiation of Human Papillomavirus Types 11, 16 and 18 Using Recombinant Virus-Like Particles," *J Gen Virol* 75:2445-2449 (1994); Touzé et al., "Prevalence of Anti-Human Papillomavirus Type 16, 18, 31, and 58 Virus-Like Particles in Women in the General Population and in Prostitutes," *J Clin Microbiol* 39(12):4344-4348 (2001); Touzé et al., "Production of Human Papillomavirus Type 45 Virus-like Particles in Insect Cells using a Recombinant Baculovirus," *FEMS Microbiol Lett* 141(1):111-116 (1996); Unckell et al., "Generation and Neutralization of Pseudovirions of Human Papillomavirus Type 33," *J Virol* 71(4): 2934-2939 (1997); Combita et al., "Serologic Response to Human Oncogenic Papillomavirus Types 16, 18, 31, 33, 39, 58 and 59 Virus-like Particles in Colombian Women with Invasive Cervical Cancer," *Internat'l J Cancer* 97(6):796-803 (2001), each of which is hereby incorporated by reference in its entirety); paramyxoviruses VLPs such as the M protein VLPs described in U.S. Patent Application Publ. No. 20070178120 to Morrison (e.g., Sendai virus VLPs, Newcastle disease virus VLPs, Mumps virus VLPs, Measles virus VLPs, Respiratory syncytial (RS) virus VLPs, rinderpest virus VLPs, distemper virus VLPs, simian parainfluenza virus (SV5) VLPs, and types I, II, and III human parainfluenza virus VLPs), which is hereby incorporated by reference in its entirety; influenza VLPs such as the VLPs disclosed in U.S. Patent Application Publ. No. 20080031895 to Galarza et al. or U.S. Patent Application Publ. No. 20060263804 to Robinson et al., each of which is hereby incorporated by reference in its entirety; buccal disease virus VLPs such as the VLPs disclosed in U.S. Patent Application Publ. No. 20070212375 to Caston et al., which is hereby incorporated by reference in its entirety; coronoavirus VLPs such as the E and M protein VLPs described in Fischer et al., "Analysis of Constructed E Gene Mutants of Mouse Hepatitis Virus Confirms a Pivotal Role for E Protein in Coronavirus Assembly," *J Virol* 72:7885-7894 (1998); Vennema et al., "Nucleocapsid-independent Assembly of Coronavirus-like Particles by Co-expression of Viral Envelope Protein Genes," *EMBO J* 15:2020-2028 (1996), each of which is hereby incorporated by reference in its entirety; chimeric coronavirus-SARS antigen VLPs such as those described in U.S. Patent Application Publ. No. 20060257852 to Rappuoli et al., which is hereby incorporated by reference in its entirety; and calicivirus VLPs such as the calicivirus coat protein VLPs described in U.S. Patent Application Publ. No. 20060172287 to Virgin et al., which is hereby incorporated by reference in its entirety.

The sensor chip arrays of the present invention are intended to include any two or more distinct VLPs or capsid fragments, including three or more distinct VLPs or capsid fragments, four or more distinct VLPs or capsid fragments, five or more distinct VLPs or capsid fragments, etc. It is contemplated that the VLPs or capsid fragments presented on the surface of the sensor chip can be any combination of VLPs or capsid fragments that are either used in a vaccine together or any combination of VLPs or capsid fragments that mimic the virus(es) for which a vaccine is given. For example, many vaccines are intended to immunize against multiple strains of virion, in which case the sensor chip should be able separately to detect immune response to each of the virion for which the vaccine is administered. It is also contemplated that a sensor chip may contain VLPs bound to one discrete location and capsid fragments bound to another discrete location.

As will be appreciated by those of skill in the art, the amount of VLP or capsid fragment bound to each discreet location on the chip can be optimized based on the surface area of the location where detection is to occur. By way of example, it is believed that optimal results can be achieved with a concentration of VLP or capsid fragment per location of about 100 fg/mm$^2$ to about 100 ng/mm$^2$, preferably about 1 pg/mm$^2$ to about 10 ng/mm$^2$.

VLPs or capsid fragments can be coupled to the sensor surface using any suitable chemistry for coupling polypeptides. Several different binding chemistries are described in the above-referenced U.S. Pat. No. 7,292,349 to Miller et al., which is hereby incorporated by reference in its entirety. Preferred approaches, particularly for oxide coatings, involve imine bond formation or the use of an aminoalkyl trialkoxysilane, followed by glutaraldehyde, which affords an amino-reactive surface capable of binding the VLPs.

Binding of the VLPs or capsid fragments to each discrete location can be carried out manually or using an automated system. For manual arraying, VLP or capsid fragment solutions can be arrayed in a volume of ~1 μL at a final concentration of 0.1 to 1,000 μg/mL, more preferably 1-100 μg/mL, after a 1:1 dilution from a 2×stock (in modified phosphate-buffered saline ("MPBS")) into a solution containing 10% glycerol and 0.01% Tween-20. After incubating for 10 minutes in an ambient environment, the chips can be immersed in a solution of blocking buffer (1 mg/mL bovine serum albumin ("BSA") in Hepes buffered saline ("HBS")) for 45 minutes and then rinsed with MPBS buffer containing an additional 3 mM EDTA and 0.005% Tween-20 ("MPBS-ET"). For automated arraying, the VLPs or capsid fragments can be arrayed by robotically printing using a Virtek ChipWriter Pro or equivalent device at a final concentration of 0.1 to 1,000 μg/mL, more preferably 1-100 μg/mL, after a 1:1 dilution from a 2×stock (in MPBS) into a solution containing 0.01-1% (v/v) 12-crown-4 ether in MPBS. After incubating for 60 minutes at 70° F. and 70% relative humidity in the microarray chamber, the chips can be immersed in a solution of blocking buffer (300 μg/mL BSA in HBS) for 60 minutes and then rinsed with MPBS-ET.

Once the array is prepared, the sensor chip can be exposed to serum samples obtained from individuals (or diluted serum samples), and then the presence (or absence) of one or more antibodies for a particular VLP can be determined based on the detection of a change (or lack of change) in the detector output following exposure of the sensor chip to the serum sample. As is well known in the art, the absence of a detectable result does not necessarily mean that the antibodies are not present but rather that they are below detectable limits and, therefore, are not likely to be present. The image capture can be achieved by any of the detection systems described above, but preferably via an image array detector that captures an image of at least a substantial portion of the surface of the chip. For arrays of hundreds to hundreds of thousands of probes, an automated chip reader can be programmed to assess the change in reflectivity for each spot on an array based on the captured image.

As used herein, the individual from which serum samples are obtained can be any animal that is susceptible to infection by a particular virus, including humans and non-human primates, livestock, domesticated animals, and wild animals. Screening of livestock is particularly desired, because it is useful for monitoring the spread of viruses by wildlife. The serum sample can be obtained from both living individuals and a corpse post-mortem.

The arrays of the present invention are particularly useful for screening the efficacy of a vaccine. Basically, the array is preferably used to screen pre- and post-immunization serum obtained from individuals to whom a vaccine has been administered. Following adequate time to allow for an immune response, post-immunization samples can be obtained and then screened against the array of the present invention. Dilution of the serum sample, typically from about 1:20 to about 1:2500, can be optimized based on the amount of VLP (or capsid fragment) loaded onto each discrete location of the array and the desired detection range. Nevertheless, following exposure of the sample to the array, detection of antibody-VLP reactivity can be assessed using the detection system employed to read the sensor chip surface by AIR, SPR, BASI, ellipsometry, etc. A quantitative measurement of the immunoreactivity can be assessed.

If desired or required, sensitivity can be further enhanced by introduction of a secondary antibody, for example an antibody specific for IgG.

Further analysis can include, without limitation, ELISA, PCR, realtime-PCR, mass spectrometry, and liquid chromatography-NMR spectroscopy. Moreover, after detecting the presence of an antibody during use of the chip, the antibody itself can be dissociated from the VLP or capsid fragment to which it was bound during use of the device. Dissociation can be achieved by any of a variety of ways including, without limitation, a glycine solution at low pH, a low pH water solution, a high pH water solution, a detergent solution (with low, moderate, or high concentrations), a low concentration denaturant solution (e.g., urea). After dissociation, the antibody (now free from the chip surface) can be recovered and then analyzed, if desired. Depending on the approach of subsequent down-stream analyses, it is possible to use the eluted samples directly or following one or more steps for concentration of the antibodies of interest.

Once the sensor chip is cleared of previously bound antibodies, the sensor chip can be re-used to screen other serum samples for the presence of anti-VLP antibodies.

EXAMPLES

The present invention may be further illustrated by reference to the following examples.

Materials and Methods for Examples 1-3
Chemicals and Materials

The following chemicals were purchased from Sigma Aldrich and used without further purification: γ-aminopropyl triethoxysilane (APTES), N,N-dimethylformamide (DMF), Tween-20, glycerol, bovine serum albumin (BSA), and buffer salts. Acetone and methanol were purchased from VWR, hydrochloric acid and hydrofluoric acid were purchased from Mallinckrodt, and benzene 1,4-diisothiocyanate was purchased from Alfa Aesar. Anti-fluorescein was purchased from Rockland Immunochemicals. Silicon wafers with approximately 1400 Å of thermally grown silicon dioxide were acquired from the Rochester Institute of Technology.

Chip Functionalization

Silicon wafers were manually diced into 2 cm×1 cm chips, and individual chips had their oxide thicknesses finely tuned to 1380 Å using successive rounds of dilute hydrofluoric acid washes. The oxide thickness of each chip was verified by spectroscopic ellipsometry (J. A. Woollam M2000). Etched chips were then washed in a 1:1 solution of hydrochloric acid:methanol for 30 minutes (Cras et al., "Comparison of Chemical Cleaning Methods of Glass in Preparation for Silanization," *Biosens Bioelectron* 14:683-688 (1999), which is hereby incorporated by reference in its entirety). After thorough washing in glass distilled deionized water (ddH$_2$O) and drying under a stream of nitrogen, the chips were submerged in a solution of APTES (0.25% v/v APTES in 4.75% ddH$_2$O and 95% acetone) for 15 minutes. After successive washes in ddH$_2$O, the chips were dried under a stream of nitrogen and cured in an oven at 100° C. for 15 minutes. Upon cooling to room temperature, a solution of benzene 1,4-diisothiocyanate (0.5% w/v in DMF) was added to the chips for 30 minutes. The chips were then thoroughly washed with acetone and dried under a stream of nitrogen.

Array Fabrication and Experimentation

VLPs corresponding to HPV genotypes 11 and 16 (HVP11 and HPV16, respectively) were diluted in a buffered saline solution (MPBS; 10 mM Na$_2$HPO$_4$, 10 mM NaH$_2$PO$_4$, 150 mM NaCl, pH 7.2) containing arraying additives (5% glycerol and 0.05% Tween-20) to concentrations suitable for arraying (10 μg/mL to 100 μg/mL). Likewise, anti-fluorescein was diluted to 20 μg/mL. Arrays were created manually by pipetting 1 μL of antibody solutions in a defined pattern of spots. Once the full array was prepared, the chips were incubated at room temperature for 30 minutes. The wet chips were then immediately immersed into a blocking solution containing 200 µg/mL BSA in HBS (20 mM HEPES, 150 mM NaCl, pH 7.2). After blocking for one hour, the chips were rinsed with ddH$_2$O, blotted at an edge to remove excess liquid, and had target solutions directly applied. Target proteins, a monoclonal antibody to HPV11 or mouse ascites fluid raised against HPBV16, were diluted 1:200 in MPBS supplemented with an additional 3 mM EDTA and 0.005% Tween-20 (MPBS-ET). These target solutions were allowed to incubate on each chip for 60 minutes. Furthermore, a negative control chip was exposed to MPBS-ET alone. All chips were then washed with ddH$_2$O and dried under a stream of nitrogen before imaging.

Image Acquisition and Data Analysis

Chips were mounted onto a bench-top reflectometer as described previously (Mace et al., "A Theoretical and Experimental Analysis of Arrayed Imaging Reflectometry as a Sensitive Proteomics Technique," *Anal Chem* 78:5578-5583 (2006), which is hereby incorporated by reference in its entirety) and images were acquired at an exposure time of 20 ms. Images were then loaded into ImageJ (Abramoff et al., "Image Processing with ImageJ," *Biophotonics Int* 11:36-42 (2004), which is hereby incorporated by reference in its entirety) to analyze the reflectance values from each spot in the array by manually selecting each spot and calculating an intensity histogram profile. These intensity data were then imported into Origin (v7.0, OriginLab), and the profiles were truncated to remove the high intensity aberrations resulting from the outer "coffee stain" ring. The resultant profiles were then fit to a normal distribution and the mean intensity value was utilized as the characteristic parameter for the spot. The signal change for each spot in the array was computed by comparing the intensity values for the experimental chip (exposed to sample) to the corresponding spot on the control chip (exposed to MPBS-ET only). All values were normalized with respect to the intrachip control probe (anti-fluorescein).

Dynamic Light Scattering

As a model particle, HPV16 VLPs were diluted to a concentration of 100 µg/mL in MPBS with and without arraying additives, and dynamic light scattering (DLS) measurements were acquired on a Malvern Zetasizer Nano (Malvern Instruments). A non-negative least-squares algorithm was employed to analyze the homogeneity of the VLP population.

Example 1

Oxide Layer Thickness and VLP Deposition Density

Figure 5:
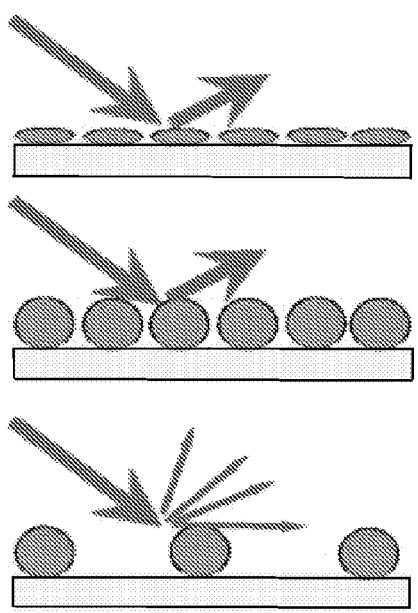
FIG. 5 illustrates models for immobilization of human papillomavirus ("HPV") VLPs on the surface of a sensor chip. Three hypothetical cases were considered, depending on the behavior of the VLP.

As a first step towards the creation of AIR chips capable of detecting anti-HPV antibodies, an assessment was made of appropriate materials conditions (oxide layer thickness and VLP deposition density) to allow production of chips with the desired null-reflectivity condition fulfilled. Dynamic light scattering measurements revealed that the population of HPV16/VLPs in solution was monodisperse, and the average calculated particle diameter varied only slightly with respect to the buffer conditions utilized: particles solubilized in MPBS alone had a measured diameter of 50 nm, while particles in MPBS supplemented with glycerol and Tween-20 had a measured diameter of 47 nm. This slight discrepancy is attributed to the differences in viscosity and refractive index, parameters required to calculate the hydrodynamic radius of a particle from the measured diffusion coefficient using the Stokes-Einstein Relation, between the two buffer formulations. Given the large size of the VLPs, there was some concern at the outset regarding the possibility that particles would scatter, rather than being well-behaved in the assay system. AIR relies on the creation of a smooth (ideally, atomically flat) antireflective coating. A close-packed monolayer of proteins immobilized on an AIR chip can approximate this (d<<λ, FIG. 5). An additional complication with regard to VLPs is that they are hollow, and potentially subject to deformation on drying. Thus, it was difficult to predict a priori whether VLPs would behave like protein monolayers (d<<λ), as 50 nm close-packed spherical objects (d<λ, rough "layer"), or as isolated discrete objects (d<λ) capable of scattering. These three possible outcomes are illustrated in FIG. 5.

Example 2

Model for HPV VLP Probes

Figure 6:
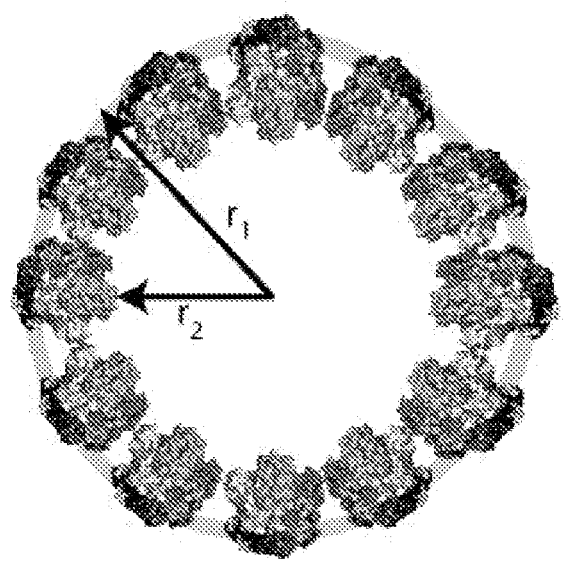
FIG. 6 shows a model for HPV16 VLP based on the dimensions of the pentameric L1 protein as determined by X-ray crystallography (PDB ID: 2R5H; rendered using MacPYMOL).

To begin to address this question, as well as determine the optimum oxide thickness needed for AIR chip fabrication, the VLP was modeled as a hollow sphere with outer radius $r_1$=25 nm and inner radius $r_2$=15 nm (FIG. 6). This model was based on X-ray crystallographic analysis of the L1 protein, which indicated a longest dimension of the protein of 10 nm (Bishop et al., "Crystal Structures of Four Types of Human Papillomavirus L1 Capsid Proteins: Understanding the Specificity of Neutralizing Monoclonal Antibodies," *J Biol Chem* 282: 31803-31811 (2007), which is hereby incorporated by reference in its entirety). Using this model, 78% of the volume of the VLP consists of protein, while 22% consists of buffer. Assuming the interior of the VLP is filled with a saline buffer and the refractive index of a protein is 1.5 (Tronin et al., "Orientational Distributions for Cytochrome C on Polar & Nonpolar Soft Surfaces by Polarized Total Internal Reflection Fluorescence," *Biophys J* 82:996-1003 (2002), which is hereby incorporated by reference in its entirety), one then arrives at an approximate refractive index for the particle of 1.46. Employing these data combined with previously measured values for the thickness of APTES and glutaraldehyde coupling layers in simulations of AIR chip behavior, a desired starting oxide thickness of 1380 Å was selected for initial experimental work.

Example 3

Optimization of VLP Immobilization Conditions

Figure 7:
FIG. 7 shows optimization of VLP immobilization conditions (raw image). Top row: HPV11 VLP; bottom row: HPV16 VLP. Columns (left to right) correspond to 100 µg/mL of VLP, respectively.

Results for the optimization of VLP immobilization conditions are shown in FIG. 7. HPV11 VLPs were slightly more well-behaved in this assay than HPV16 VLPs; whether this is due to intrinsic properties of the individual VLPs themselves, or due to the particular preparation methods is uncertain. In the end, 20 µg/mL was chosen as the concentration for further experiments, as higher concentrations gave too much signal over background. These results also suggest that VLPs behave more like a close-packed layer than like isolated particles (see FIG. 5). This is a gratifying result, and indicates that other virus-sized particles should be well-behaved components of AIR chips.

Example 4

Detection of Anti-HPV Antibodies

Figure 8:
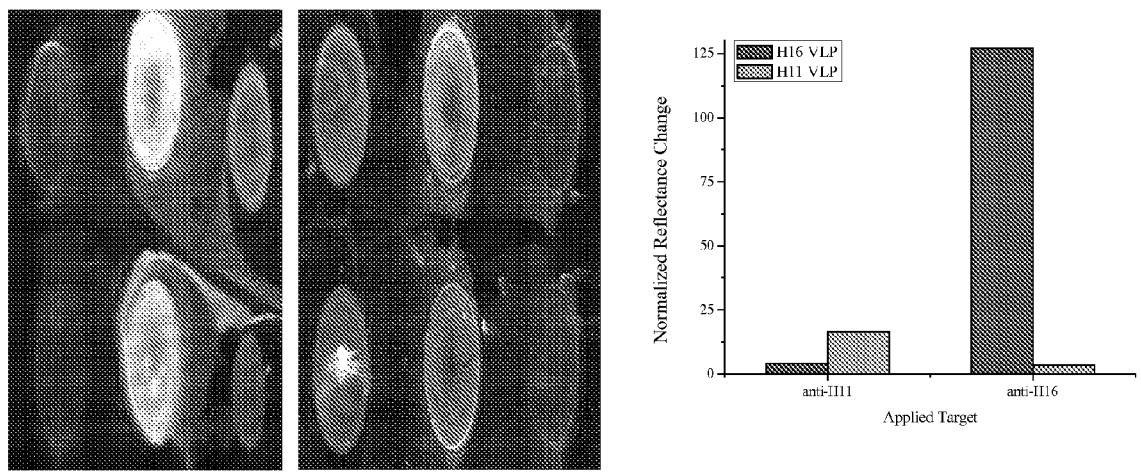
FIG. 8 shows an image of a chip (left) following exposure to 1:200 dilution of mouse ascites fluid containing antibodies specific to HPV16 VLP. The leftmost column of spots are comprised of HPV11 VLP, the center column of spots are HPV16 VLP, and the rightmost column of spots are antifluorescein. The center image shows the corresponding background chip, and the bar graph on the right illustrates the results.

Once optimized, the ability of these chips to detect anti-HPV antibodies in purified form and derived from diluted mouse ascites fluid was examined. In both cases, stock antibody solution concentrations were unknown; these were diluted 1:200 in MPBS-ET based on preliminary trial-and-error experiments. Results of these experiments are shown in FIG. 8. Gratifyingly, it was possible to differentiate anti-HPV11 and anti-HPV16 based on the immobilized VLP; very little cross-reactivity was observed. As is evident from the experimental image (FIG. 8, left), some nonspecific binding to the chip surface occurred, but only in areas of the chip suffering from "smearing" (inadvertent probe immobilization) during the washing process. Nonspecific binding is of course a particular concern for "label-free" assays; in this case, it was well below a level that would interfere with the ability to observe the desired target. It is also noted that the observed inhomogeneity in spot morphology can be potentially ameliorated through the incorporation of various additives in the protein-spotting solution. This has been examined in another context with considerable success (Mace et al., "Investigation of Non-nucleophilic Additives for Reduction of Morphological Anomalies in Protein Arrays," *Langmuir* 24:12754-12757 (2008) and U.S. Provisional Patent Application Ser. No. 61/101,831 to Mace et al., each of which is hereby incorporated by reference in their entirety).

Preliminary construction and operation of an AIR sensor for antibodies to viral proteins has been demonstrated. Importantly, despite the large size (approximately 50 nm) of the HPV-derived VLPs employed as probe molecules, the anti-reflectance condition required for AIR was still satisfied. These data demonstrate that VLP-derived antigen arrays using the AIR detection system may prove suitable for surveillance applications and for monitoring vaccine efficacy. Furthermore, this proof-of-principle sets the stage for the use of AIR antigen arrays for monitoring antibody response to a host of other viruses.

Example 5

Detection of Anti-HPV Antibodies

Pre- and post-inoculation serum samples from patients receiving the Gardisil® vaccine will be obtained and then exposed to sensor chips that include VLPs against HPV-6, -11, -16, and -18. The extent of the immune response against each component of the vaccine will be assessed via AIR, although it is expected that the HPV-6 and HPV-11 results will be complicated by the cross-reactivity of these genotypes.

Example 6

Detection of Anti-Norwalk Virus Antibodies

Pre- and post-inoculation serum samples from patients receiving a Norwalk virus vaccine will be obtained and then exposed to sensor chips that include VLPs against the Norwalk virus. The extent of the immune response against Norwalk virus will be assessed via AIR as described in Example 4.

Example 7

Detection of Anti-Influenza Virus Antibodies

Pre- and post-inoculation serum samples from human patients receiving the Novavax H5N1 VLP vaccine will be obtained and then exposed to sensor chips that include VLPs against the H5N1 strain of influenza virus. These VLPs include HA, NA, and M1 proteins. The extent of the immune response against H5N1 virus will be assessed via AIR as described in Example 4.

Example 8

Detection of Anti-Ebola Virus Antibodies

Pre- and post-inoculation serum samples from non-human primates receiving an Ebola VLP vaccine will be obtained and then exposed to sensor chips that include VLPs against the Ebola virus. These VLPs include glycoprotein and VP40 protein (Warfield et al., "Filovirus-like Particles as Vaccines and Discovery Tools," *Expert Rev Vaccines* 4(3):429-440 (2005), which is hereby incorporated by reference in its entirety). The extent of the immune response against Ebola virus will be assessed via AIR as described in Example 4.

Example 9

Detection of Anti-Marburg Virus Antibodies

Pre- and post-inoculation serum samples from non-human primates receiving a Marburg VLP vaccine will be obtained and then exposed to sensor chips that include VLPs against the Marburg virus. These VLPs include glycoprotein and VP40 protein, and optionally VP24, VP30, and VP35 protein (Warfield et al., "Filovirus-like Particles as Vaccines and Discovery Tools," *Expert Rev Vaccines* 4(3):429-440 (2005), which is hereby incorporated by reference in its entirety). The extent of the immune response against Marburg virus will be assessed via AIR as described in Example 4.

Although the preliminary experiments described in Example 4 have been conducted using AIR as a label-free sensor platform, it should be appreciated by those of skill in the art that AIR is merely a preferred sensing platform because of its simplicity, sensitivity, and adaptability to large arrays of probe molecules (in this example, VLPs). Indeed, use of an arrays sensor suitable for use in surface plasmon resonance ("SPR") detection systems, Brewster Angle Straddle Interferometry ("BASI"), ellipsometry, and any other label-free or fluorescence labeled array techniques is contemplated.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

What is claimed:

1. An arrayed imaging reflectometry (AIR) sensor chip suitable for the detection of antiviral immune responses comprising:
    a multilayer substrate comprising a surface and virus-like particles (VLPs) or viral capsid (CA) fragments from different viral strains or isolates, wherein said VLPs or CA fragments from each individual isolate or strain are covalently attached to the chip surface at different locations;

wherein said VLPs or CA fragments retain conformational epitopes that are capable of binding to antiviral antibodies;

wherein said surface with VLPs or CA fragments covalently attached at the different locations forms a coating on the chip surface that results in destructive interference of polarized light illuminating said surface at an appropriate incident angle and wavelength in the absence of antibody binding; and wherein exposure of the surface to a sample comprising antiviral antibodies produces a detectable change in reflectance upon antigen-antibody binding.

2. The sensor chip according to claim 1, wherein the VLPs or CA fragments each comprise an immunodominant epitope of their respective native viral strain.

3. The sensor chip according to claim 1, wherein the VLPs are selected from the group consisting of papillomavirus VLPs, paramyxoviruses VLPs, influenza VLPs, coronoavirus VLPs, chimeric coronavirus-SARS antigen VLPs, calicivirus VLPs, HIV VLPs, and combinations thereof.

4. The sensor chip according to claim 1, wherein the VLPs or CA fragments are covalently attached to the substrate via an imine bond or a glutaraldehyde linker.

5. The sensor chip according to claim 1, wherein each of said locations comprises a concentration of VLPs or CA fragments of about 100 fg/mm$^2$ to about 100 ng/mm$^2$.

6. The sensor chip according to claim 1, wherein reflectivity is less than about $10^{-5}$ in the absence of antibody binding to the VLPs or CA fragments.

7. A method for detecting antiviral antibodies using arrayed imaging reflectometry (AIR), said method comprising:

providing a sensor chip according to claim 1;

contacting the sensor chip with a sample under conditions that permit specific antiviral antibody binding to the VLPs or CA fragments present on the chip surface;

rinsing the sensor chip to remove any unbound antibody; and detecting light reflected off the surface of the chip under conditions effective to identify antiviral antibody-antigen binding.

8. The method according to claim 7, wherein the sample is obtained from a human, non-human primate, domesticated animal, or wild animal.

9. The method according to claim 7, wherein said detecting comprises:

measuring light reflected from the chip and providing an output identifying the VLPs or CA fragments bound by an antibody of the sample based on the measured reflected light.

10. The method according to claim 8, wherein the measuring the reflected light further comprises capturing an image of at least a substantial portion of the surface of the chip.

* * * * *